United States Patent [19]
McLaughlin

[11] Patent Number: 5,638,453
[45] Date of Patent: Jun. 10, 1997

[54] TRANSDUCER ENHANCED STETHOSCOPE

[76] Inventor: Bruce E. McLaughlin, 1426 Green Oak Rd., Vista, Calif. 92083

[21] Appl. No.: 593,060

[22] Filed: Jan. 29, 1996

[51] Int. Cl.$^6$ ........................................... A61B 7/04
[52] U.S. Cl. ........................... 381/67; 128/680; 128/689; 128/675; 128/715
[58] Field of Search ......................... 381/67; 128/680, 128/689, 700, 675, 715

[56] References Cited

U.S. PATENT DOCUMENTS

| | | | |
|---|---|---|---|
| 4,129,125 | 12/1978 | Lester et al. | 128/715 |
| 4,320,767 | 3/1982 | Villa-Real | 128/680 |
| 4,898,179 | 2/1990 | Sirota | 128/700 |
| 4,972,841 | 11/1990 | Iguchi | 128/715 |

*Primary Examiner*—Forester W. Isen

[57] ABSTRACT

A transducer enhanced stethoscope including a head piece that has an ear piece at each end and is connected to bifurcated flexible tubing. The bifurcated tubing is integral a flexible short tube. Included is a pickup head that has a top face, a bottom face and a peripheral wall with a connector projecting therefrom. The top face has a pair of temperature sensors fixedly attached. Each temperature sensor is capable of measuring skin temperature for displaying on a top readout screen. The bottom face has a pulse sensor. The pulse sensor is capable of measuring blood flow rate for displaying on a bottom readout screen. A battery is sealed within the pickup head by a battery door that is accessible along the bottom face. Lastly, an elongated flexible tubing is coupled to the connector of the pickup head. The elongated tubing is capable of transmitting acoustical sound waves from the pickup head to the head piece.

7 Claims, 3 Drawing Sheets

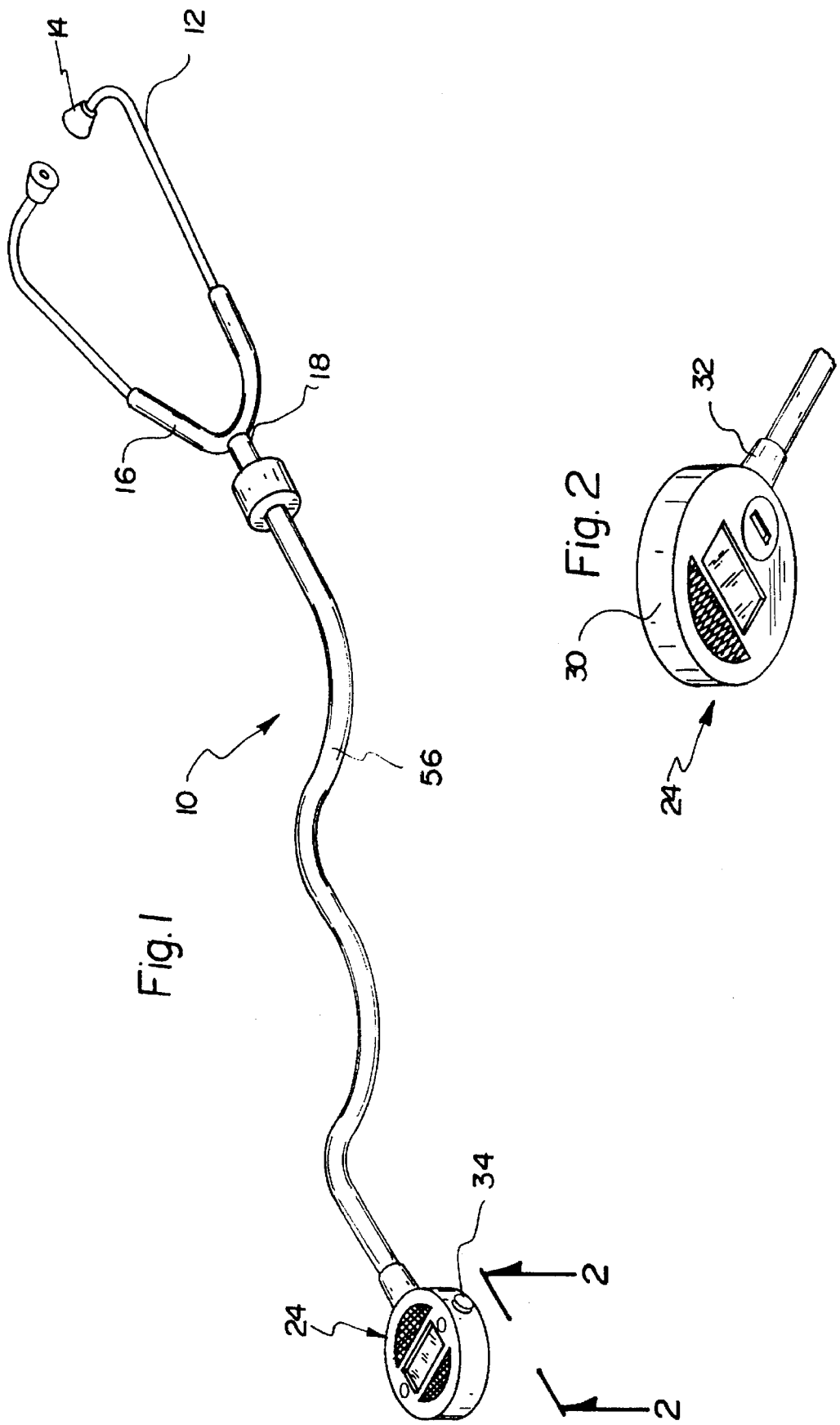

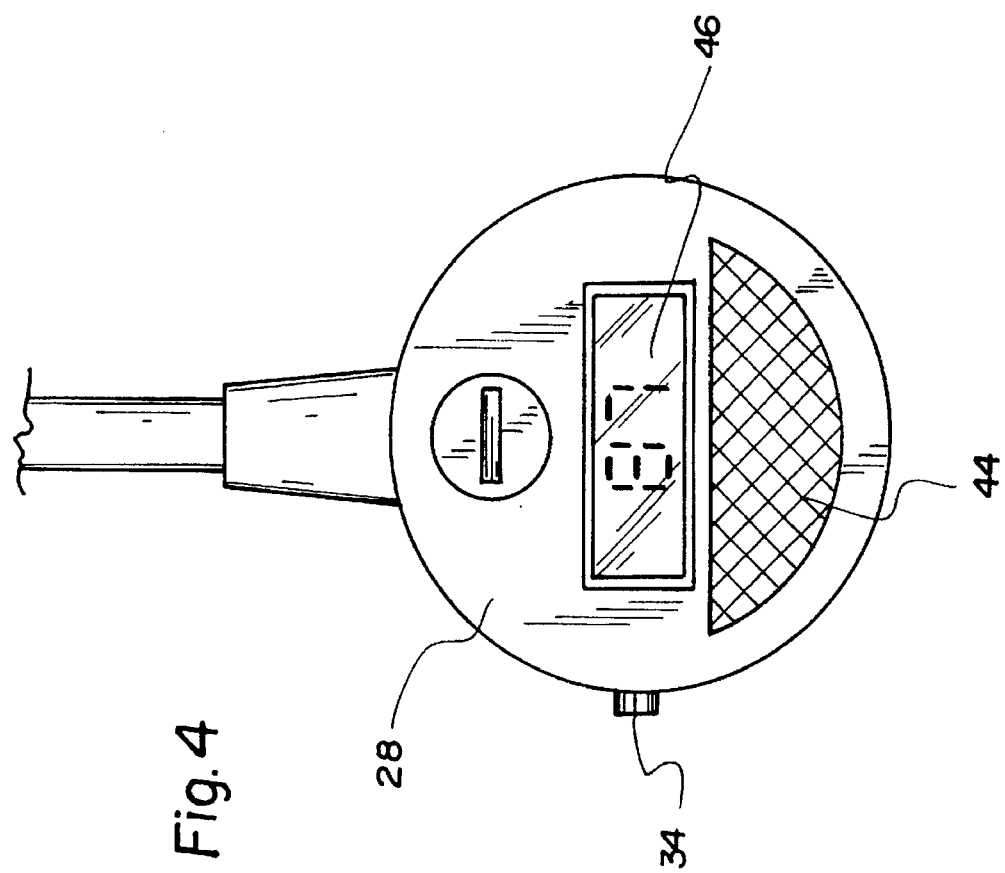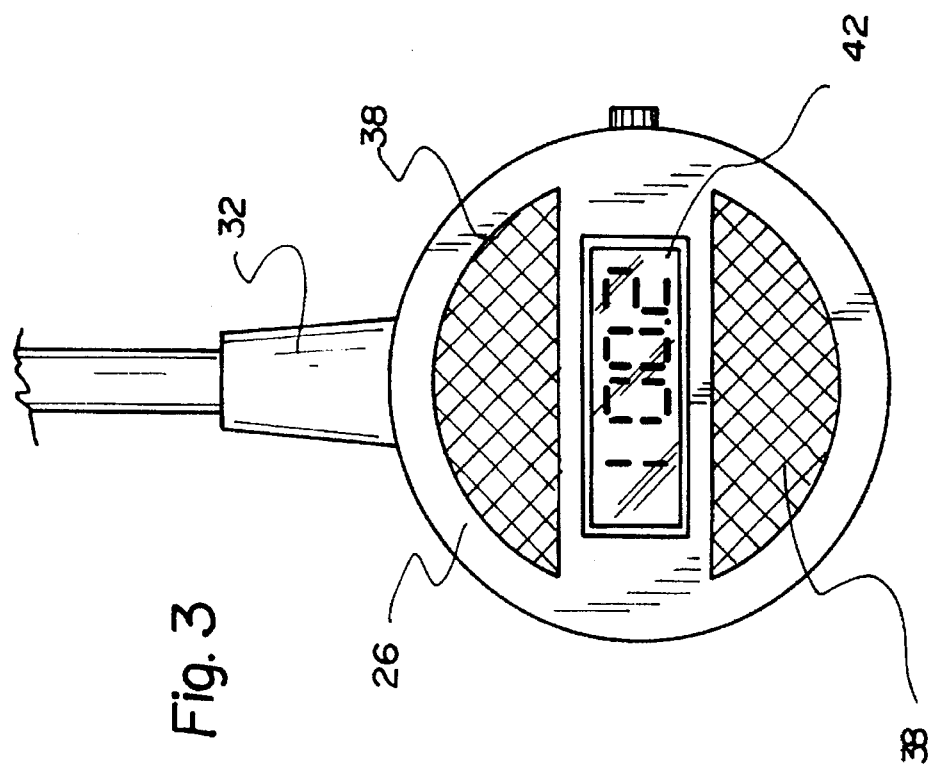

TRANSDUCER ENHANCED STETHOSCOPE

BACKGROUND OF THE INVENTION

1. Field of the Invention

The present invention relates to a transducer enhanced stethoscope and more particularly pertains to providing a stethoscope with a transducer for indicating the body temperature and pulse rate of a human subject.

2. Description of the Prior Art

The use of a stethoscope is known in the prior art. More specifically, stethoscopes heretofore devised and utilized for the purpose of transmitting sounds from a body are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 4,072,822 to Yamada discloses a two-way stethoscope for direct and amplified sound. U.S. Pat. No. 5,252,787 to Moore and Harley discloses a stethoscope. U.S. Pat. No. 4,783,813 to Kempka discloses an electronic sound amplifier stethoscope with visual heartbeat and blood flow indicator. U.S. Pat. No. 4,903,794 to Kilppert et al. discloses an acoustical amplifying stethoscope. U.S. Pat. No. 3,444,954 to Scanlon discloses a stethoscope. Lastly, U.S. Pat. No. 5,295,489 to Bell and McKay discloses an endotracheal tube/stethoscope/transmitter combination.

While these devices fulfill their respective, particular objectives and requirements, the aforementioned patents do not describe transducer enhanced stethoscope that allows the heart rate and skin temperature of a body to be determined with the present invention, in addition, enhancing the audio carried from the pickup head of the present invention.

In this respect, the transducer enhanced stethoscope according to the present invention substantially departs from the conventional concepts and designs of the prior art, and in doing so provides an apparatus primarily developed for the purpose of providing a stethoscope with a transducer for indicating the body temperature and pulse rate of a human subject.

Therefore, it can be appreciated that there exists a continuing need for a new and improved transducer enhanced stethoscope which can be used for providing a stethoscope with a transducer for indicating the body temperature and pulse rate of a human subject. In this regard, the present invention substantially fulfills this need.

SUMMARY OF THE INVENTION

In view of the foregoing disadvantages inherent in the known types of stethoscopes now present in the prior art, the present invention provides an improved transducer enhanced stethoscope. As such, the general purpose of the present invention, which will be described subsequently in greater detail, is to provide a new and improved transducer enhanced stethoscope and method which has all the advantages of the prior art and none of the disadvantages.

To attain this, the present invention essentially comprises a binaural head piece that has an ear piece at each end and is connected to bifurcated flexible tubing. The bifurcated tubing is integral a flexible short tube. The short tube is perpendicular the bifurcated tubing. A generally cylindrical pickup head is included. The pickup head has a top face, a bottom face and a peripheral wall. The pickup head has a cylindrical connector and a reset button projecting from the peripheral wall. The cylindrical connector and the reset button are spaced one from another along the peripheral wall. The top face of the pickup head has a pair of semi-circular temperature sensors fixedly attached. Each temperature sensor is capable of measuring skin temperature and displaying it on a top readout screen. The top readout screen is positioned between the pair of sensors on the top face. The bottom face of the pickup head has a semi-circular pulse sensor. The pulse sensor is capable of measuring blood flow rate and displaying the rate on a bottom readout screen. The bottom readout screen is adjacent the pulse sensor. The reset button is capable of resetting the bottom readout screen after each use of the pulse sensor. A battery is housed within the pickup head. The battery is sealed within the pickup head by a battery door. The battery door is threadably attached to the bottom face of the pickup head, and near the bottom readout screen. The battery is capable of providing power for the top readout screen and the bottom readout screen. An elongated flexible tubing is coupled to the connector of the pickup head at one end. The elongated tubing has a sound amplification mechanism at another end. The elongated tubing is capable of transmitting acoustical sound waves from the pickup head to the amplification mechanism. Lastly, the amplification mechanism has a housing that is coupled with the short tubing. The amplification mechanism is powered by the battery housed in the pickup head. Whereby, the pickup head is capable of transmitting audible sound waves into the amplification mechanism for receipt by the head piece.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved transducer enhanced stethoscope which has all of the advantages of the prior art stethoscopes and none of the disadvantages.

It is another object of the present invention to provide a new and improved transducer enhanced stethoscope which may be easily and efficiently manufactured and marketed.

It is further object of the present invention to provide a new and improved transducer enhanced stethoscope which is of durable and reliable constructions.

An even further object of the present invention is to provide a new and improved transducer enhanced stethoscope which is susceptible of a low cost of manufacture with regard to both materials and labor, and which accordingly is then susceptible of low prices of sale to the consuming public, thereby making such transducer enhanced stethoscope economically available to the buying public.

Still yet another object of the present invention is to provide a new and improved transducer enhanced stethoscope which provides in the apparatuses and methods of the prior art some of the advantages thereof, while simultaneously overcoming some of the disadvantages normally associated therewith.

Even still another object of the present invention is to provide a transducer enhanced stethoscope for providing a stethoscope with a transducer for indicating body temperature and pulse rate of a human subject.

Lastly, it is an object of the present invention to provide a new and improved transducer enhanced stethoscope including a head piece that has an ear piece at each end and is connected bifurcated flexible tubing. The bifurcated tubing is integral a flexible short tube. Included is a pickup head that has a top face, a bottom face and a peripheral wall with a connector projecting therefrom. The top face has a pair of temperature sensors fixedly attached. Each temperature sensor is capable of measuring skin temperature for displaying on a top readout screen. The bottom face has a pulse sensor. The pulse sensor is capable of measuring blood flow rate for displaying on a bottom readout screen. A battery is sealed within the pickup head by a battery door that is accessible along the bottom face. Lastly, an elongated flexible tubing is coupled to the connector of the pickup head. The elongated tubing is capable of transmitting acoustical sound waves from the pickup head to the head piece.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is a perspective view of the preferred embodiment of the transducer enhanced stethoscope constructed in accordance with the principles of the present invention.

FIG. 2 is a bottom isometric vie of the pickup head of the present invention.

FIG. 3 is a frontal elevational view of the pickup head in an operable configuration.

FIG. 4 is a bottom elevational vie of the pickup head of the present invention.

The same reference numerals refer to the same parts through the various Figures.

DESCRIPTION OF THE PREFERRED EMBODIMENT

Figure 6:
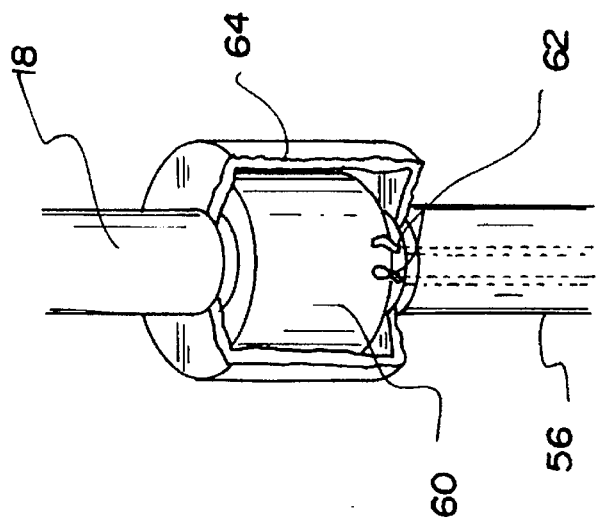
FIG. 6 is a fragmentary view of the sound amplification mechanism of the present invention.

With reference now to the drawings, and in particular to FIG. 1 thereof, the preferred embodiment of the new and improved transducer enhanced stethoscope embodying the principles and concepts of the present invention and generally designated by the reference numeral 10 will be described.

The present invention, the transducer enhanced stethoscope 10 is comprised of a plurality of components. Such components in their broadest context include a head piece, a sound amplifier, tubing and a pickup head. Such components are individually configured and correlated with respect to each other so as to attain the desired objective.

Specifically, the present invention includes a binaural head piece 12 having an ear piece 14 at each end. The head piece, as seen in FIG. 1, is connected to a bifurcated flexible tubing 16. The bifurcated tubing is integral a flexible short tue 18. The short tube is perpendicular the bifurcated tubing. These components of the present invention are conventional in the art as used currently in the medical arena. The bifurcated tubing may be made from rubber, plastic or other material currently being used. The head piece may be made of a rigid plastic, flexible plastic or metal. Normally, the head piece is constructed of metal.

Also, a generally cylindrical pickup head 24 is provided. The pickup head, as shown in FIG. 2, has a top face 26, a bottom face 28 and a peripheral wall 30. The pickup head is formed of a rigid plastic with conventional internal structure, that includes a sound chamber. The pickup head has a cylindrical connector 32 and a reset button 34 projecting from the peripheral wall. The cylindrical connector and the reset button are spaced one from the other along the peripheral wall 18.

As best illustrated in FIG. 3, the top face 26 of the pickup head 24 has a pair of semi-circular temperature sensors 38 that are fixedly attached. Each sensor may be made of thermal active liquid crystal. The present invention, as shown with this application, uses a transducer. Each temperature sensor is capable of measuring skin temperature and displaying it on a top readout screen 42. The top readout screen is an LED indicator. The top readout screen is positioned between the pair of sensors on the top face. The top readout screen, clears automatically when the sensors are removed from the skin.

FIG. 4 shows the bottom face 28 of a pickup head having a semi-circular pulse sensor 44. The sensor uses a transducer to determine the pulse of the body. The sensor replaces the old method of placing two fingers over the veins of the wrist. The pulse sensor is capable of measuring blood rate for displaying on a bottom readout screen 46. The bottom readout screen is adjacent the pulse sensor. The bottom readout screen includes a time date function. The reset button 34 is capable of resetting the bottom readout screen after each use of the pulse sensor. The reset button controls the time date readout on the bottom readout screen.

Figure 5:
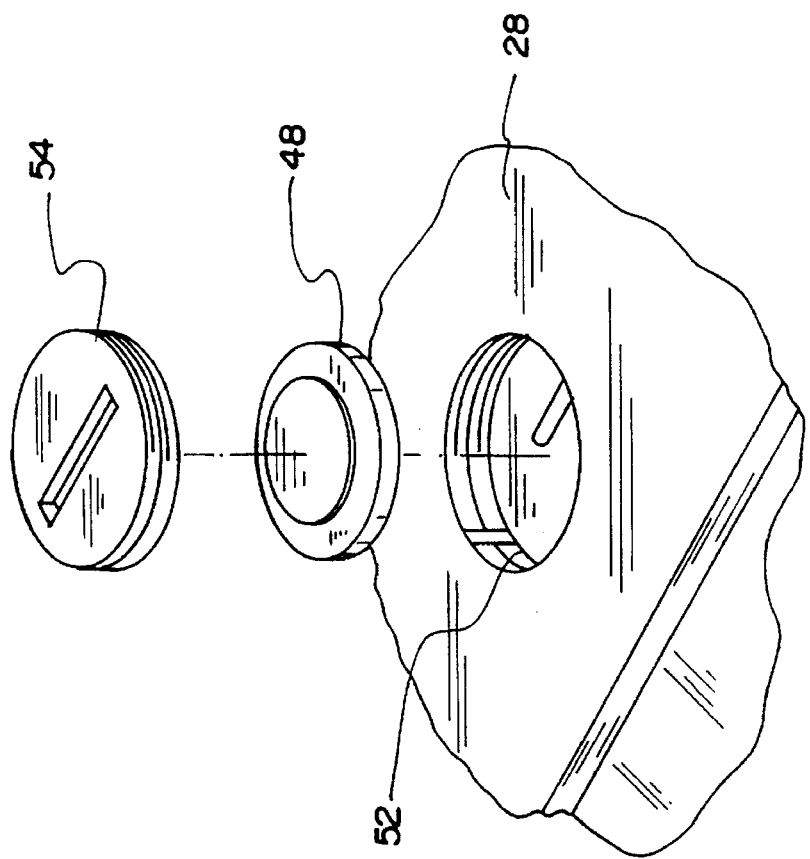
FIG. 5 is an exploded view of the battery, battery door and the pickup head of the present invention.

A battery 48 is housed within the pickup head. The battery is a disc type battery, like those used commercially in wrist watches and pocket calculators. The battery is positioned in a battery chamber 52 of the pickup head. The battery chamber is accessed through the bottom face. The battery is sealed within the pickup head by a battery door 54 of FIG. 5. The battery door is threadably attached to the bottom face of the pickup head near the bottom readout screen 46. The battery provides power for the top readout screen and the bottom readout screen.

Additionally, an elongated flexible tubing 56 is included and coupled to the connector 32 of the pickup head at one end. As shown in FIG. 6, the elongated tubing has a sound amplification mechanism 60 at another end. The elongated tubing is made from the same material used to make the short tubing. The elongated tubing is capable of transmitting acoustical sound waves from the pickup head 24 to the amplification mechanism.

Lastly, the amplification mechanism 60 has a pair of wires 62 extending the width of the elongated tubing and making contact with the battery 48. The amplification mechanism has a housing 64 that is coupled with the short tubing 18 and made of plastic. The amplification mechanism, that is used in the present invention, may be one of the commercially available products currently on the market. Once such amplification mechanism is known as the (miracle ear™) The amplification mechanism is powered by the battery. Whereby, the pickup head is capable of transmitting audible sound waves into the amplification mechanism for enhancing the sound waves that will be received by the head piece.

The present invention is a new and improved transducer enhanced stethoscope. The stethoscope measures skin temperature and heart rate. Also, the sound transmitted from the pickup head of the stethoscope is passed through an amplification mechanism that enhances the sound to be received. The pulse and the skin temperature, of the present invention are measured by sensors on the pickup head. The sensors for measuring skin temperature are found on the top face of the pickup head. These sensors use a transducer. The sensors for determining the pulse is located on the bottom face of the pickup head. The sound amplifier is positioned between the elongated tube and a short tube. The stethoscope of the present invention allows the collection of the heart rate and skin temperature at the pickup end of the stethoscope. The present invention, when used by medical professionals, increases the accuracy of determining the pulse of the body. Also, since skin temperature can be sometimes misleading, when determined by touch, the present invention gives you a more accurate measurement.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A new and improved transducer enhanced stethoscope for measuring skin temperature and heart rate comprising in combination:

a binaural headpiece having an ear piece at each end and being connected to bifurcated flexible tubing, the bifurcated tubing being integral a flexible short tube, the short tube being perpendicular the bifurcated tubing;

a generally cylindrical pickup head having a top face, a bottom face and peripheral wall therebetween, the pickup head having a cylindrical connector and a reset button projecting from the peripheral wall, the cylindrical connector and the reset button being spaced one from the other along the peripheral wall;

the top face of the pickup head having a pair of semi-circular temperature sensors fixedly attached thereto, each temperature sensor being capable of measuring skin temperature for displaying on a top readout screen, the top readout screen being positioned between the pair of sensors on the top face, the bottom face of the pickup head having a semi-circular pulse sensor, the pulse sensor being capable of measuring blood flow rate for displaying on a bottom readout screen, the bottom readout screen being adjacent the pulse sensor, the reset button being capable of resetting the bottom readout screen after each use of the pulse sensor;

a battery being housed within the pickup head, the battery being sealed within the pickup head by a battery door, the battery door being threadedly attached to the bottom face of the pickup head near the bottom readout screen, the battery being capable of providing power for the top readout screen and the bottom readout screen;

an elongated flexible tubing being coupled to the connector of the pickup head at one end, the elongated tubing having a sound amplification mechanism at another end, the elongated tubing being capable of transmitting acoustical sound waves from the pickup head to the amplification mechanism; and the amplification mechanism having a housing being coupled with the short tubing, the amplification mechanism being powered by the battery housed within the pickup head, whereby the pickup head being capable of transmitting audible sound waves into the amplification mechanism for receipt by the headpiece.

2. A transducer enhanced stethoscope comprising:

a headpiece having an ear piece at each end and being connected to bifurcated flexible tubing, the bifurcated tubing being integral a flexible short tube;

a pickup head having a top face, a bottom face and peripheral wall with a connector projecting therefrom, the top face having a pair of temperature sensors fixedly attached thereto, each temperature sensor being capable of measuring skin temperature for displaying on a top readout screen, the bottom face having a pulse sensor, the pulse sensor being capable of measuring blood flow rate for displaying on a bottom readout screen;

a battery being sealed within the pickup head by a battery door accessible along the bottom face; and an elongated flexible tubing being coupled to the connector of the pickup head and being capable of transmitting acoustical sound waves from the pickup head to the head piece.

3. The transducer enhanced stethoscope as set forth in claim 2 wherein the pickup head has a reset button projecting from the peripheral wall and being spaced from the connector.

4. The transducer enhanced stethoscope as set forth in claim 3 wherein the top readout screen being positioned between the pair of sensors on the top face, the bottom readout screen being adjacent the pulse sensor, and the reset button being capable of resetting the bottom readout screen after each use of the pulse sensor.

5. The transducer enhanced stethoscope as set forth in claim 2 wherein the battery door being threadedly attached to pickup head at the bottom face and near the bottom readout screen, the battery being capable of providing power for the top readout screen and the bottom readout screen.

6. The transducer enhanced stethoscope as set forth in claim 2 wherein a sound amplification mechanism being attached to one end of the elongated tubing and the short tubing, the short tube being perpendicular the bifurcated tubing and coupled to a housing of the amplification mechanism.

7. The transducer enhanced stethoscope as set forth in claim 6 wherein the amplification mechanism being powered by the battery housed within the pickup head, whereby the pickup head being capable of transmitting audible sound waves into the amplification mechanism for magnification.

* * * * *